United States Patent
Itai et al.

(10) Patent No.: US 9,974,860 B2
(45) Date of Patent: May 22, 2018

(54) AQUEOUS SOLUTION FORMULATION AND METHOD FOR MANUFACTURING SAME

(71) Applicant: Akiko ITAI, Tokyo (JP)

(72) Inventors: Akiko Itai, Tokyo (JP); Ryoichi Tomita, Tokyo (JP); Tomoyuki Fujikawa, Tokyo (JP)

(73) Assignee: AKIKO ITAI, Tokyo (JP)

( * ) Notice: Subject to any disclaimer, the term of this patent is extended or adjusted under 35 U.S.C. 154(b) by 0 days. days.

(21) Appl. No.: 14/917,638

(22) PCT Filed: Sep. 11, 2014

(86) PCT No.: PCT/JP2014/074065
§ 371 (c)(1),
(2) Date: Mar. 9, 2016

(87) PCT Pub. No.: WO2015/037659
PCT Pub. Date: Mar. 19, 2015

(65) Prior Publication Data
US 2016/0220680 A1     Aug. 4, 2016

(30) Foreign Application Priority Data
Sep. 13, 2013   (JP) .................. 2013-191192

(51) Int. Cl.
*A61K 31/166* (2006.01)
*A61K 47/28* (2006.01)
(Continued)

(52) U.S. Cl.
CPC ............... *A61K 47/28* (2013.01); *A61K 9/08* (2013.01); *A61K 31/166* (2013.01);
(Continued)

(58) Field of Classification Search
None
See application file for complete search history.

(56) References Cited
U.S. PATENT DOCUMENTS
3,331,874 A    7/1967   Stecker
3,332,996 A    7/1967   Zerweck et al.
(Continued)

FOREIGN PATENT DOCUMENTS
JP    2006-160696 A    6/2006
JP    2011-140470 A    7/2011
(Continued)

OTHER PUBLICATIONS
Kolar (Fluid Phase Equilibria, 2002; 194-197:771-782).*
(Continued)

Primary Examiner — Marcos L Sznaidman
Assistant Examiner — Rayna Rodriguez
(74) Attorney, Agent, or Firm — Greenblum & Bernstein, P.L.C.

(57) ABSTRACT

An aqueous solution formulation containing Compound (I) can be manufactured by performing a first step of preparing a dissolution liquid obtained by dissolving a compound represented by Formula (I) below or a pharmacologically acceptable salt thereof and a compound represented by any of General Formulas (II) to (IV) below in an organic solvent, a second step of removing the organic solvent from the dissolution liquid, and a third step of adding a solution to residual substances obtained through the second step to dissolve the residual substances.

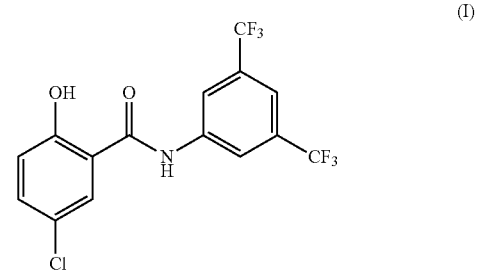

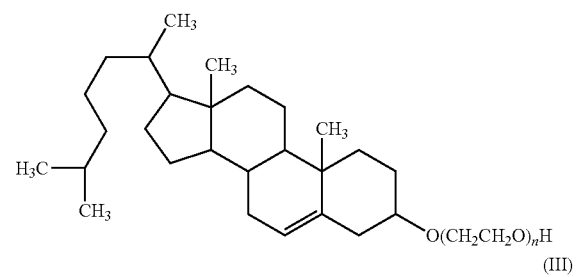

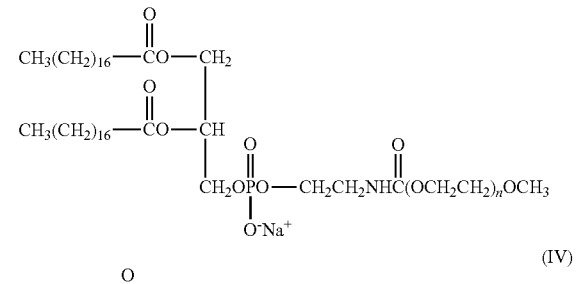

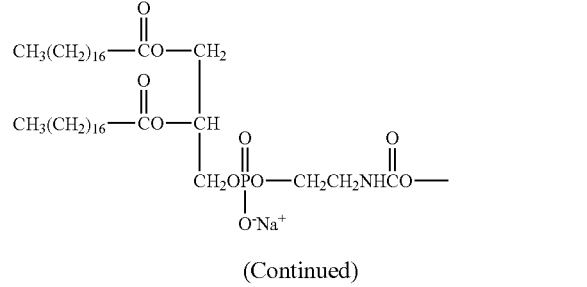

(Continued)

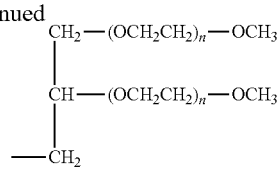

27 Claims, No Drawings

(51) Int. Cl.
  A61K 9/08    (2006.01)
  A61K 31/167  (2006.01)
  A61K 47/24   (2006.01)
  A61K 9/107   (2006.01)
(52) U.S. Cl.
  CPC ............ A61K 31/167 (2013.01); A61K 47/24
        (2013.01); A61K 9/1075 (2013.01)

(56) References Cited

U.S. PATENT DOCUMENTS

| | | |
|---|---|---|
| 2004/0259877 A1 | 12/2004 | Muto et al. |
| 2006/0014811 A1 | 1/2006 | Muto et al. |
| 2006/0019958 A1 | 1/2006 | Muto et al. |
| 2006/0035944 A1 | 2/2006 | Muto et al. |
| 2006/0089395 A1 | 4/2006 | Muto et al. |
| 2006/0094718 A1 | 5/2006 | Muto et al. |
| 2006/0100257 A1 | 5/2006 | Muto et al. |
| 2006/0111409 A1 | 5/2006 | Muto et al. |
| 2006/0122243 A1 | 6/2006 | Muto et al. |
| 2007/0042997 A1 | 2/2007 | Itai et al. |
| 2007/0185059 A1 | 8/2007 | Muto et al. |
| 2007/0185110 A1 | 8/2007 | Muto et al. |
| 2007/0254956 A1 | 11/2007 | Shudo et al. |
| 2008/0090779 A1 | 4/2008 | Muto et al. |
| 2008/0234233 A1 | 9/2008 | Muto et al. |
| 2008/0249071 A1 | 10/2008 | Muto et al. |
| 2008/0311074 A1 | 12/2008 | Muto et al. |
| 2008/0318956 A1 | 12/2008 | Muto et al. |
| 2009/0130214 A1 | 5/2009 | Couvreur et al. |
| 2009/0239868 A1 | 9/2009 | Muto et al. |
| 2010/0062437 A1 | 3/2010 | Lawrence |
| 2010/0113770 A1 | 5/2010 | Muto et al. |
| 2010/0234452 A1 | 9/2010 | Mian et al. |
| 2010/0274051 A1 | 10/2010 | Muto et al. |
| 2011/0142815 A1 | 6/2011 | Yu |
| 2011/0268722 A1 | 11/2011 | Siegelin et al. |
| 2012/0010178 A1 | 1/2012 | Rubin et al. |
| 2012/0183524 A1 | 7/2012 | Rahman |
| 2012/0190565 A1 | 7/2012 | Lisanti et al. |
| 2012/0277249 A1 | 11/2012 | Andersson et al. |
| 2013/0209578 A1 | 8/2013 | Borden et al. |
| 2013/0243694 A1 | 9/2013 | Ito et al. |
| 2014/0163088 A1 | 6/2014 | Yu |
| 2014/0322705 A1 | 10/2014 | Lisanti et al. |

FOREIGN PATENT DOCUMENTS

| | | |
|---|---|---|
| JP | 2012-102107 A | 5/2012 |
| JP | 2013-199476 A | 10/2013 |
| WO | 2006/013873 A1 | 2/2006 |
| WO | 2008/094410 A2 | 7/2008 |
| WO | 2008/133884 A2 | 11/2008 |
| WO | 2009/006555 A2 | 1/2009 |
| WO | 2009/074809 A1 | 6/2009 |
| WO | 2009/082514 A1 | 7/2009 |
| WO | 2010/000903 A2 | 1/2010 |
| WO | 2010/048273 A2 | 4/2010 |
| WO | 2010/096574 A1 | 8/2010 |
| WO | 2010/099731 A1 | 9/2010 |
| WO | 2010/106082 A1 | 9/2010 |
| WO | 2011/133879 A2 | 10/2011 |
| WO | 2012/019284 A1 | 2/2012 |
| WO | 2012/024612 A1 | 2/2012 |
| WO | 2012/148799 A1 | 11/2012 |

OTHER PUBLICATIONS

Yasuyuki Onai et al., "Inhibition of IκB phosphorylation in cardiomyocytes attenuates myocardial ischemia/reperfusion injury", Cardiovasc. Res., 63(1), p. 51-59 (2004).
Junji Kamon et al., "A novel IKKβ inhibitor stimulates adiponectin levels and ameliorates obesity-linked insulin resistance", Biochemical and Biophysical Research Communications, 323(1), p. 242-248 (2004).
Akane Tanaka et al., "A novel NF-κB inhibitor, IMD-0354, suppresses neoplastic proliferation of human mast cells with constitutively activated c-kit receptors", Blood, 105(6), p. 2324-2331 (2005).
Akane Tanaka et al., "A New IκB Kinase β Inhibitor Prevents Human Breast Cancer Progression through Negative Regulation of Cell Cycle Transition", Cancer Res., 66(1), p. 419-426 (2006).
Mami Inayama et al., "A Novel IκB Kinase-β Inhibitor Ameliorates Bleomycin-induced Pulmonary Fibrosis in Mice", American Journal of respiratory and critical care medicine, 173(9), p. 1016-1022 (2006).
Yasuyuki Onai et al., "Inhibition of NF-κB improves left ventricular remodeling and cardiac dysfunction after myocardial infarction", Am. J. Physiol. Heart Circ. Physiol., 292(1), H530-538 (2007).
Akane Tanaka et al., "Topical Application with a New NF-κB Inhibitor Improves Atopic Dermatitis in NC/NgaTnd Mice", Journal of Investigative Dermatology, 127(4), p. 855-863 (2007).
Ayako Yanai et al., "Activation of IκB kinase β and NF-κB Is Essential for Helicobacter pylori-Induced Chronic Gastritis in Mongolian Gerbils", Infect. Immun., 76(2), p. 781-787 (2008).
Takanori Ochiai et al., "Inhibition of IκB kinase β restrains oncogenic proliferation of pancreatic cancer cells", J. Med. Dent. Sci., 55(1), p. 49-59 (2008).
Yoku Hayakawa et al., "Effectiveness of IjB kinase inhibitors in murine colitis-associated tumorigenesis", J. Gastroenterol., 44(9), p. 935-943 (2009).
Akemi Sugita et al., "Antiallergic and Anti-Inflammatory Effects of a Novel IκB Kinase β Inhibitor, IMD-0354, in a Mouse Model of Allergic Inflammation", Int. Arch. Allergy Immunol., 148(3), p. 186-198 (2009).
A. Matsuda et al., "A novel NF-κB inhibitor improves glucocorticoid sensitivity of canine neoplastic lymphoid cells by up-regulating expression of glucocorticoid receptors", Research in Veterinary Science, 89(3), p. 378-382 (2010).
H. Ogawa et al., "IκB kinase β inhibitor IMD-0354 suppresses airway remodelling in a Dermatophagoides pteronyssinus-sensitized mouse model of chronic asthma", Clinical & Experimental Allergy, 41(1), p. 104-115 (2011).
Seiichi Fukuda et al., "Aldosterone-induced kidney injury is mediated by NFκB activation", Clin. Exp. Nephrol., 15(1), p. 41-49 (2011).
Jun-ichi Suzuki et al., "Novel IκB kinase inhibitors for treatment of nuclear factor-κ-B-related diseases", Expert. Opim. Investig. Drugs, 20(3), p. 395-405 (2011).
Shin Uota et al., "An IκB kinase 2 inhibitor IMD-0354 suppresses the survival of adult T-cell leukemia cells", Cancer Sci., 103(1), p. 100-106 (2012).
Christoph Thiemermann, "Inhibition of the activation of nuclear factor kappa B to reduce myocardial reperfusion injury and infarct size", Cardiovascular Research, 63(1), p. 8-10 (2004).
Ming Fan et al., "Nuclear Factor-κB and Manganese Superoxide Dismutase Mediate Adaptive Radioresistance in Low-Dose Irradiated Mouse Skin Epithelial Cells", Cancer Res., 67(7), p. 3220-3228 (2007).

(56) References Cited

OTHER PUBLICATIONS

Patnaik MM et al., "Kit: molecule of interest for the diagnosis and treatment of mastocytosis and other neoplastic disorders", Curr. Cancer Drug Targets, 7(5), p. 492-503 (2007).

Tetsuro Ozawa et al., "Thymic stomal lymphopoietin secretion of synovial fibroblasts is positively and negatively regulated by Toll-like receptors/nuclear factor-κB pathway and interferon-γ/dexamethasone", Mod. Rheumatol., 17(6), p. 459-463 (2007).

Wei Zhang et al., "Down-Regulation of α1-Adrenoceptor Expression by Lipid-Soluble Smoke Particles through Transcriptional Factor Nuclear Factor-κB Pathway", Basic Clin. Pharmacol. Toxicol., 101(6), p. 401-406 (2007).

Masanori Wako et al., "Mechanism of Signal Transduction in Tumor Necrosis Factor-Like Weak Inducer of Apoptosis-Induced Matrix Degradation by MMP-3 Upregulation in Disc Tissues", Spine (phila Pa 1976), 33(23), p. 2489-2494 (2008).

Ning Cao et al., "NF-κB-Mediated HER2 Overexpression in Radiation-Adaptive Resistance", Radial. Res., 171(1), p. 9-21 (2009).

Rickard Norden et al., "Activation of host antiviral RNA-sensing factors necessary for herpes simplex virus type 1-activated transcription of host cell fucosyltransferase genes FUT3, FUT5, and FUT6 and subsequent expression of sLex in virus-infected cells", Glycobiology, 19(7), p. 776-788 (2009).

Saravanan Rajendrasozhan et al., "Targeted disruption of NF-κB1 (p50) augments cigarette smoke-induced lung inflammation and emphysema in mice: a critical role of p50 in chromatin remodeling", Am. J. Physiol. Lung Cell Mol. Physiol., 298(2), L197-209 (2010).

Ryuta Kamekura et al., "Thymic stromal lymphopoietin induces tight junction protein claudin-7 via NF-κB in dendritic cells", Histochem. Cell Biol., 133(3), p. 339-348 (2010).

Jian-Pu Zheng et al., "NF-kappaB signaling mediates vascular smooth muscle endothelin type B receptor expression in resistance arteries", European Journal of Pharmacology, 637(1-3), p. 148-154 (2010).

Qing-Wen Chen et al., "Cigarette Smoke Extract Promotes Human Vascular Smooth Muscle Cell Proliferation and Survival through ERK1/2- and NF-κB-Dependent Pathways", Scientific World Journal, 10, p. 2139-2156 (2010).

Hardip Sandhu et al., "Upregulation of contractile endothelin type B receptors by lipid-soluble cigarette smoking particles in rat cerebral arteries via activation of MAPK", Toxicology and Applied Pharmacology, 249(1), p. 25-32 (2010).

Giovanni Forte et al., "CI-IB-MECA enhances TNF-α release in peritoneal macrophages stimulated with LPS", Cytokine, 54(2), p. 161-166 (2011).

Maddahi et al., "The role of tumor necrosis factor-α and TNF-α receptors in cerebral arteries following cerebral ischemia in rat", Journal of Neuroinflammation, 8, 107 (2011).

Y. Liu et al., "Involvement of the NF-κB pathway in multidrug resistance induced by HBx in a hepatoma cell line", Journal of Viral Hepatitis, 18(10), e439-446 (2011).

Jue Wei et al., "IkB kinase-beta inhibitor attenuates hepatic fibrosis in mice", World J. Gastroenterol., 17(47), p. 5203-5213 (2011).

Jordan C. Bell et al., "Regulation of Cytochrome P450 4F11 by Nuclear Transcription Factor-κB", Drug Metab. Dispos., 40(1), p. 205-211 (2012).

Wei Zhanga et al.,"Activation of nuclear factor-κB pathway is responsible for tumor necrosis factor-α-induced up-regulation of endothelin B2 receptor expression in vascular smooth muscle cells in vitro", Toxicology Letters, 209(2), p. 107-112 (2012).

International Search Report issued with respect to application No. PCT/JP2014/074065, dated Jan. 6, 2015.

International Preliminary Report on Patentability issued with respect to application No. PCT/JP2014/074065, dated Mar. 15, 2016.

\* cited by examiner

AQUEOUS SOLUTION FORMULATION AND METHOD FOR MANUFACTURING SAME

TECHNICAL FIELD

The present invention relates to an aqueous solution formulation containing N-[3,5-bis(trifluoromethyl)phenyl]-5-chloro-2-hydroxybenzamide as an efficacious component, and a method for manufacturing the same.

BACKGROUND ART

It has been known that a compound (referred to as Compound (I) hereinafter) represented by Formula (I) below:

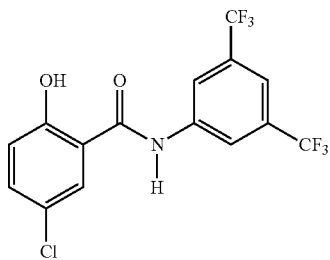

is useful for preventing or improving various diseases and is useful in various formulations (see Patent Documents 1 to 40 and Non-Patent Documents 1 to 35).

CITATION LIST

Patent Documents

Patent Document 1: U.S. Pat. No. 3,331,874
Patent Document 2: U.S. Pat. No. 3,332,996
Patent Document 3: U.S. Patent Application Publication No. 2004/0259877
Patent Document 4: U.S. Patent Application Publication No. 2008/0318956
Patent Document 5: U.S. Patent Application Publication No. 2010/0274051
Patent Document 6: U.S. Patent Application Publication No. 2008/0249071
Patent Document 7: U.S. Patent Application Publication No. 2006/0122243
Patent Document 8: U.S. Patent Application Publication No. 2008/0090779
Patent Document 9: U.S. Patent Application Publication No. 2007/0185110
Patent Document 10: U.S. Patent Application Publication No. 2007/0185059
Patent Document 11: U.S. Patent Application Publication No. 2006/0111409
Patent Document 12: U.S. Patent Application Publication No. 2006/0019958
Patent Document 13: U.S. Patent Application Publication No. 2006/0100257
Patent Document 14: U.S. Patent Application Publication No. 2006/0089395
Patent Document 15: U.S. Patent Application Publication No. 2008/0311074
Patent Document 16: U.S. Patent Application Publication No. 2006/0014811
Patent Document 17: U.S. Patent Application Publication No. 2006/0035944
Patent Document 18: U.S. Patent Application Publication No. 2008/0234233
Patent Document 19: U.S. Patent Application Publication No. 2007/0042997
Patent Document 20: U.S. Patent Application Publication No. 2007/0042997
Patent Document 21: U.S. Patent Application Publication No. 2007/0254956
Patent Document 22: U.S. Patent Application Publication No. 2009/0239868
Patent Document 23: U.S. Patent Application Publication No. 2006/0094718
Patent Document 24: U.S. Patent Application Publication No. 2010/0113770
Patent Document 25: International Publication WO 2008/041066
Patent Document 26: International Publication WO 2008/094410
Patent Document 27: International Publication WO 2008/133884
Patent Document 28: International Publication WO 2009/006555
Patent Document 29: International Publication WO 2009/074809
Patent Document 30: International Publication WO 2009/082514
Patent Document 31: International Publication WO 2010/000903
Patent Document 32: International Publication WO 2010/048273
Patent Document 33: International Publication WO 2010/096574
Patent Document 34: International Publication WO 2010/096574
Patent Document 35: International Publication WO 2010/099731
Patent Document 36: International Publication WO 2010/106082
Patent Document 37: International Publication WO 2011/133879
Patent Document 38: International Publication WO 2012/019284
Patent Document 39: International Publication WO 2012/024612
Patent Document 40: International Publication WO 2006/013873

Non-Patent Documents

Non-Patent Document 1: Cardiovasc. Res., 63(1), p. 51-59 (2004).
Non-Patent Document 2: Biochem. Biophys. Res. Commun., 323(1), p. 242-248 (2004).
Non-Patent Document 3: Blood, 105(6), p. 2324-2331 (2005).
Non-Patent Document 4: Cancer Res., 66(1), p. 419-426 (2006).
Non-Patent Document 5: Am. J. Respir. Crit. Care Med., 173(9), p. 1016-1022 (2006).
Non-Patent Document 6: Am. J. Physiol. Heart Circ. Physiol., 292(1), H530-538 (2007).
Non-Patent Document 7: J. Invest. Dermatol., 127(4), p. 855-863 (2007).
Non-Patent Document 8: Infect. Immun., 76(2), p. 781-787 (2008).

Non-Patent Document 9: J. Med. Dent. Sci., 55(1), p. 49-59 (2008).
Non-Patent Document 10: J. Gastroenterol., 44(9), p. 935-943 (2009).
Non-Patent Document 11: Int. Arch. Allergy Immunol., 148(3), p. 186-198 (2009).
Non-Patent Document 12: Res. Vet. Sci., 89(3), p. 378-382 (2010).
Non-Patent Document 13: Clin. Exp. Allergy, 41(1), p. 104-115 (2011).
Non-Patent Document 14: Clin. Exp. Nephrol., 15(1), p. 41-49 (2011).
Non-Patent Document 15: Expert. Opin. Investig. Drugs, 20(3), p. 395-405 (2011).
Non-Patent Document 16: Cancer Sci., 103(1), p. 100-106 (2012).
Non-Patent Document 17: Cadiovasc. Res., 63(1), p. 8-10 (2004).
Non-Patent Document 18: Cancer Res., 67(7), p. 3220-3228 (2007).
Non-Patent Document 19: Curr. Cancer Drug Targets, 7(5), p. 492-503 (2007).
Non-Patent Document 20: Mod. Rheumatol., 17(6), p. 459-463 (2007).
Non-Patent Document 21: Basic Clin. Pharmacol. Toxicol., 101(6), p. 401-406 (2007).
Non-Patent Document 22: Spine (phila Pa 1976), 33(23), p. 2489-2494 (2008).
Non-Patent Document 23: Radiat. Res., 171(1), p. 9-21 (2009).
Non-Patent Document 24: Glycobiology, 19(7), p. 776-788 (2009).
Non-Patent Document 25: Am. J. Physiol. Lung Cell Mol. Physiol., 298(2), L197-209 (2010).
Non-Patent Document 26: Histochem. Cell Biol., 133(3), p. 339-348 (2010).
Non-Patent Document 27: Eur. J. Pharmacol., 637(1-3), p. 148-154 (2010).
Non-Patent Document 28: Scientific World Journal, 10, p. 2139-2156 (2010).
Non-Patent Document 29: Toxicol. Appl. Pharmacol., 249 (1), p. 25-32 (2010).
Non-Patent Document 30: Cytokine, 54(2), p. 161-166 (2011).
Non-Patent Document 31: J. Neuroinflammation, 8, 107 (2011).
Non-Patent Document 32: J. Viral Hepat., 18(10), e439-446 (2011).
Non-Patent Document 33: World J. Gastroenterol., 17(47), p. 5203-5213 (2011).
Non-Patent Document 34: Drug Metab. Dispos., 40(1), p. 205-211 (2012).
Non-Patent Document 35: Toxicol. Lett., 209(2), p. 107-112 (2012).

SUMMARY OF INVENTION

Technical Problem

However, Compound (I) above has poor water solubility, thus making it difficult to manufacture an aqueous solution formulation containing Compound (I).

The object of the present invention is to provide an aqueous solution formulation containing Compound (I) and a method for manufacturing the same.

Solution to Problem

As a result of having conducted various studies to solve the foregoing problems, the inventors of the present invention found that when Compound (I) and a compound represented by General Formula (II), (III), or (IV) below were dissolved in an organic solvent and then the organic solvent was removed from this dissolution liquid, the obtained residual substances could be dissolved in water or an aqueous solution, that is, an aqueous solution formulation containing Compound (I) could be manufactured, thus allowing the present invention to be achieved.

Specifically, the present invention includes the following aspects:

[1] a method for manufacturing an aqueous solution formulation including a first step of preparing a dissolution liquid obtained by dissolving a compound represented by Formula (I) below or a pharmacologically acceptable salt thereof and a compound represented by any of General Formulas (II) to (IV) below in an organic solvent, a second step of removing the organic solvent from the dissolution liquid, and a third step of adding a solution to residual substances obtained through the second step to dissolve the residual substances;

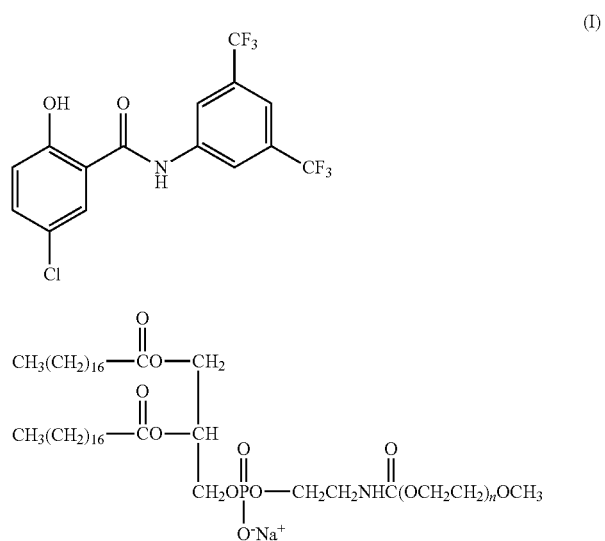

-continued

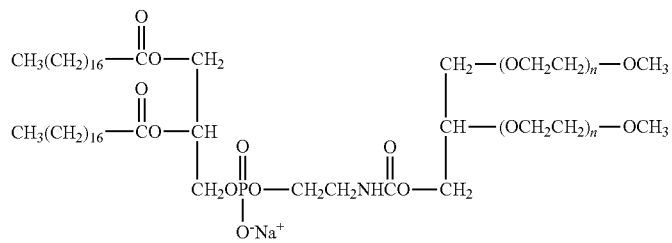
(IV)

[2] the method for manufacturing an aqueous solution formulation according to [1], wherein n in the compound represented by General Formula (II) is 14 or 37;

[3] the method for manufacturing an aqueous solution formulation according to [1], wherein n in the compound represented by General Formula (III) is 46;

[4] the method for manufacturing an aqueous solution formulation according to [1], wherein n in the compound represented by General Formula (IV) is 46; and

[5] an aqueous solution formulation obtained through the method for manufacturing an aqueous solution formulation according to any of [1] to [4] above.

Advantageous Effects of Invention

According to the present invention, it is possible to provide an aqueous solution formulation containing Compound (I) and a method for manufacturing the same.

DESCRIPTION OF EMBODIMENTS

Hereinafter, an embodiment of the present invention, which was achieved based on the above-mentioned findings, will be described in detail by way of working examples. Unless otherwise stated in the working examples, commercially available reagent kits and measurement apparatuses are used in accordance with their protocols included therewith.

It should be noted that the purposes, characteristics, advantages, and ideas of the present invention are clear to a person skilled in the art by descriptions in the present specification, and a person skilled in the art can easily reproduce the present invention according to the descriptions in the present specification. An embodiment and specific working examples of the present invention described below represent preferred aspects of the present invention and are shown for illustration or explanation, and the present invention is not limited thereto. It is clear to a person skilled in the art that various alterations and modifications may be carried out based on the descriptions in the present specification within the intention and the scope of the present invention disclosed in the present specification.

An aqueous solution formulation of the present invention, that is, an aqueous solution formulation containing Compound (I) as an efficacious component, can be manufactured by a method including a first step of preparing a dissolution liquid obtained by dissolving Compound (I) or a pharmacologically acceptable salt thereof and a compound represented by General Formula (II), (III), or (IV) in an organic solvent, a second step of removing the organic solvent from the dissolution liquid, and a third step of adding a solution to residual substances obtained through the second step to dissolve the residual substances.

Compound (I) can be manufactured in accordance with the method described in U.S. Patent Application Publication No. 2004/0259877, for example. Pharmacologically acceptable salts of Compound (I) can be manufactured with a method that is widely used in the art. Examples of the pharmacologically acceptable salts of Compound (I) include metal salts such as a lithium salt, a sodium salt, a potassium salt, a magnesium salt, and a calcium salt and salts of ammonium such as an ammonium salt, a methylammonium salt, a dimethylammonium salt, a trimethylammonium salt, and dicyclohexylammonium salt.

Although there is no particular limitation on the compound represented by General Formula (II) as long as the compound has an average molecular weight of 1000 to 2000, that is, n (the average number of polyethylene glycol (PEG) units included in the compound) is an integer from 14 to 37, it is preferable to use the compound having an average molecular weight of 1000 or 2000, that is, the compound in which n is 14 or 37.

Although there is no particular limitation on the compound represented by General Formula (III) as long as the compound includes polyethylene glycol having an average molecular weight of 1000 to 2000, that is, n is an integer from 22 to 46, it is preferable to use the compound including polyethylene glycol having an average molecular weight of 2000, that is, the compound in which n is 46. It should be noted that the compound represented by General Formula (III) can be manufactured in accordance with the method described in U.S. Pat. No. 6,679,822.

Although there is no particular limitation on the compound represented by General Formula (IV) as long as the compound includes polyethylene glycol having an average molecular weight of 1000 to 2000, that is, n is an integer from 22 to 46, it is preferable to use the compound including polyethylene glycol having an average molecular weight of 2000, that is, the compound in which n is 46.

There is no particular limitation on the organic solvent as long as Compound (I) or a pharmacologically acceptable salt thereof and the compound represented by General Formula (II), (III), or (IV) can be dissolved in the organic solvent. Examples of the organic solvent include primary alcohols such as methanol, ethanol, isopropanol, and tert-butanol; dimethylsulfoxide (DMSO); methyl tert-butyl ether; N,N-dimethylacetamide; N,N-dimethylformamide; acetone; N-methyl-2-pyrrolidone; tetrahydrofuran; acetonitrile; or ethyl acetate, or a mixture thereof. It is preferable to use a pharmaceutically acceptable organic solvent such as ethanol, N-methyl-2-pyrrolidone, and dimethylsulfoxide.

There is no particular limitation on the temperature at which Compound (I) or a pharmacologically acceptable salt thereof and a compound represented by General Formula (II), (III), or (IV) are dissolved in the organic solvent as long as Compound (I) or a pharmacologically acceptable salt thereof and a compound represented by General Formula (II), (III), or (IV) can be dissolved in the organic solvent. The dissolution temperature is in a temperature range of 50 to 60° C., for example.

Examples of a method for removing the organic solvent from the dissolution liquid in which Compound (I) or a pharmacologically acceptable salt thereof and the compound represented by General Formula (II), (III), or (IV) are dissolved include known methods such as evaporation to dryness, drying, and distillation under reduced pressure.

There is no particular limitation on the solution that is added to residual substances obtained by removing the organic solvent from the above-mentioned dissolution liquid as long as the solution is pharmaceutically acceptable. Examples of the solution include water for injection (water), a physiological saline, an aqueous solution of glucose, a Ringer's solution, and a lactated Ringer's solution. It should be noted that there is no particular limitation on the temperature at which this solution is added to the residual substances to dissolve the residual substances as long as the residual substances can be dissloved in the solution. The temperature at which the residual substances are dissolved is in a range of 0 to 60° C., preferably 4 to 55° C., and more preferably room temperature (23 to 25° C.) to 55° C.

Although the aqueous solution formulation obtained through the method for manufacturing an aqueous solution formulation according to the present invention may be used in any concentration as long as the concentration is in a concentration range in which the aqueous solution formulation can be used as a formulation for injection or the like, that is, Compound (I) is dissolved at a concentration of 1 mg/mL or more, the higher-concentration aqueous solution formulation is preferable from the viewpoint of reducing the amount.

The aqueous solution formulation according to the present invention manufactured as described above is useful for preventing (including the suppression of progress/exacerbation) or improving (including medical treatment, prolongation of human life, and the like) the diseases mentioned in Patent Documents 1 to 40 and Non-Patent Documents 1 to 35 above. Examples of the diseases include autoimmune diseases, inflammatory diseases, allergic diseases, tumors, cancers, carcinomas, sarcomas, blood diseases, cardiovascular diseases, respiratory system diseases, digestive system diseases, liver diseases, lung diseases, urological diseases, endocrine diseases, metabolic diseases, eye diseases, otorhinolaryngologic diseases, skin diseases, neurological diseases, brain diseases, connective tissue diseases, musculoskeletal diseases, viral diseases, bacterial diseases, and thromboses.

Specific examples of the above-mentioned diseases include rheumatoid arthritis, osteoarthrosis, systemic lupus erythematosus, systemic sclerosis, polymyositis, Sjogren's syndrome, vasculitic syndrome, anti-phospholipid syndrome, Still's disease, Behcet's disease, periarteritis nodosa, ulcerative colitis, Crohn's disease, active chronic hepatitis, glomerulonephritis, chronic nephritis, chronic pancreatitis, gout, atherosclerosis, multiple sclerosis, vascular intima thickening, psoriasis, psoriatic arthritis, contact dermatitis, atopic dermatitis, eczema, pollenosis, urticaria, angiitis, rhinitis, dyspepsia, diarrhea, neuritis, otitis media, granulomatosis, cystitis, laryngitis, purpura, food allergy, insect allergy, drug allergy, metal allergy, anaphylactic shock, asthma, bronchitis, interstitial pneumonia, chronic obstructive pulmonary disease, chronic pulmonary thromboembolism, inflammatory colitis, insulin resistance, adiposity, diabetes mellitus, diabetic complication, nephropathy, retinopathy, cataract, neurosis, gangrene, hyperinsulinemia, arteriosclerosis, hypertension, peripheral vascular occlusion, coma, hyperlipidemia, pneumonia, Alzheimer's disease, Parkinson's disease, Huntington's disease, encephalomyelitis, epilepsy, recurrent shoulder joint dislocation, acute hepatitis, chronic hepatitis, drug-induced liver injury, alcoholic hepatitis, viral hepatitis, jaundice, liver cirrhosis, liver failure, atrial myxoma, Castleman syndrome, mesangial proliferative nephritis, tumor, solid cancer, kidney cancer, lung cancer, liver cancer, breast cancer, uterine cancer, pancreatic cancer, prostate cancer, colorectal cancer, skin cancer, ovarian cancer, cervical cancer, melanoma, sarcoma, osteosarcoma, tumor metastasis, tumor invasion, cancerous cachexia, leukemia, multiple myeloma, Lennert lymphoma, malignant lymphoma, drug-resistant tumor, brain tumor, nervous system tumor, sarcoidosis, endotoxic shock, sepsis, cytomegaloviral pneumonia, cytomegaloviral retinopathy, adenoviral cold, adenoviral pool fever, adenoviral ophthalmitis, ophthalmitis, conjunctivitis, acquired immune deficiency syndrome, uveitis, systemic inflammatory syndrome, restenosis or reocclusion after revascularization (e.g., percutaneous transluminal coronary angioplasty), ischemia-reperfusion injury, rejection after a tissue transplant, periodontal disease, alopecia, anorexia, fatigue, chronic fatigue syndrome, osteoporosis, cancer pain, organopathy, myocarditis, myositis, restenosis after a stent placement, arthritis, dermatitis, endometriosis, uterine fibroids, cardiac remodeling, vascular remodeling, bronchial remodeling, cardiac infarction, nephritis, fibrosis (e.g, pulmonary fibrosis, hepatic fibrosis, and cystic fibrosis and the like), depression, keloid, chromatosis, thrombosis, liver disorders, cerebral thrombosis, cerebral embolism, cerebral infarction, transient ischemic attack, cerebral stroke, cerebrovascular dementia, ischemic cerebrovascular disease, angina pectoris, intra-atrial thrombosis caused by atrial fibrillation, cardiac failure, ischemic heart disease, pulmonary thrombosis, pulmonary embolism, thrombotic lung disease, deep vein thrombosis (DVT), thrombophlebitis, obstructive venous disease, acute arterial occlusion, chronic arterial occlusion, obstructive peripheral arterial disease, thrombosis after bypass vascular transplant, disseminated intravascular coagulation (DIC), angiopathy, renal thrombosis, renal embolism, thrombotic renal disease, thrombotic disease, blood coagulation, ischemic diseases, heart attack, profunda thrombosis, venous thrombosis, nephrosclerosis, metabolic syndrome, aldosterone-induced tissue damage, organ failure, interstitial cystitis, prostatomegaly, amyotrophia, dysmnesia, age-related macular degeneration, lymphedema, cerebral edema, dysuria, vascular event, economy class syndrome, nonbacterial thrombotic endocarditis, infectious disease (e.g., infectious disease caused by bacteria such as *Staphylococcus aureus, S. choleraesuis, Escherichia coli* and the like), hypercholesterolemia, polycystic kidney disease, wound, decubitus, pain (e.g., lumbago, arthralgia, neuralgia, and toothache), refractory hypertension, chronic kidney disease (CKD), muscular dystrophy, mesothelioma, fever, hydrocephalus, hyperglycemic disease, memory formation failure, glaucoma, cardiogenic embolism, aneurysm, Harada's disease, nonalcoholic hepatitis, retinal vein occlusion, central serous chorioretinopathy, and premature labor. In addition, a composition for injection of the present invention can be used as an organ deterioration inhibitor during the preservation of pretransplantation organs.

It should be noted that in this specification, the term "prevention and/or improvement of tumor" or synonyms thereof include a tumoricidal effect or an anticancer effect as well as a canceration inhibitory effect with respect to tissues or cells, a tumor metastasis inhibitory effect, reinforcement of the effect of existing antitumor agents, an overcoming effect with respect to drug resistance for existing antitumor agents, a cancerous cachexia improving effect, a recurrence preventing effect, a life prolonging effect with respect to tumor patients, and the like. Moreover, the term "prevention or improvement of Alzheimer's disease" includes an amyloid β protein accumulation suppressing effect, a nerve cell death suppressing effect, an encephalatrophy suppressing effect, a neurofibrillary tangle suppressing effect, a dementia improving effect, and the like. Furthermore, the term "prevention or improvement of epilepsy" includes an effect of suppressing an epileptic fit (e.g., tonic-clonic seizure, absence seizure, and myoclonic jerk), a suppressing effect of neuronal hyper-excitability in the cerebrum, a suppressing effect of a nerve cell death in the hippocampus, and the like.

The aqueous solution formulation of the present invention may further contain one or more additives that are acceptable as components of the aqueous solution formulation in addition to the above-mentioned residual substances and solution. Examples of the additives include a buffer such as sodium phosphate; a stabilizer such as sodium pyrosulfite; an osmotic pressure-adjusting agent such as sodium chloride, mannitol, or glycerin; a soothing agent such as lidocaine; and a preservative such as phenol.

The required amount of the composition for injection of the present invention may be administered to a subject to be administered all at once, or intermittently, or continuously. One example of the continuous administration method is an instillation administration.

The composition for injection of the present invention can be preferably used for the improvement of acute diseases for which a therapeutic drug needs to be urgently administered. Examples of the diseases include cerebrovascular disorders such as cerebral stroke and ischemic heart diseases such as acute cardiac infarction. Moreover, the composition for injection of the present invention can be preferably used for the improvement of diseases for which a therapeutic drug needs to be continuously administered.

WORKING EXAMPLES

Hereinafter, the present invention will be more specifically described by way of working examples, but the scope of the present invention is not limited to the following working examples. It should be noted that in these working examples, SUNBRIGHT (registered trademark) CS-010 and CS-020 (available from NOF Corporation) were used as an example of the compound represented by General Formula (II), SUNBRIGHT (registered trademark) DSPE-020CN (available from NOF Corporation) was used as an example of the compound represented by General Formula (III), and SUNBRIGHT (registered trademark) DSPE-020GL2U (available from NOF Corporation) was used as an example of the compound represented by General Formula (IV).

Working Examples 1 to 7: Preparation of Aqueous Solution Containing Compound (I)

The drug (Compound (I)), a compound shown in the table below, and ethanol were put into a vial, and by heating them to between 55 to 60° C., the drug and the compound were completely dissolved in the ethanol (such that the resulting solution was colorless and transparent without forming a deposit and a precipitate) to prepare each dissolution solution. The content in the dissolution solution was dried up by evaporation at 60° C. for 1.5 hours. A predetermined amount of a physiological saline or water was added to the obtained residue and heated to 55° C. (in Working Example 6, the mixture was incubated at room temperature for 24 hours; in Working Example 7, the mixture was incubated at 4° C. for 72 hours), and the residue was dissolved. When visually observed, the aqueous solution in the vial contained no deposit and no precipitate and was colorless and transparent. Therefore, it was confirmed that the drug was completely dissolved, and an aqueous solution containing Compound (I) at a concentration of at least 1 mg/ml could be prepared. It should be noted that although attempts were made to use compounds other than the compounds shown in the table below to prepare an aqueous solution containing Compound (I) at a concentration of 1 mg/ml, an aqueous solution in which the drug was completely dissolved could not be prepared in the case of using compounds other than the compounds shown in the table below.

TABLE 1

| Work. Ex. | Compound Product name | Compound concentration in aqueous solution | Drug concentration in aqueous solution | Type of aqueous solution used |
|---|---|---|---|---|
| 1 | DSPE-020CN | 15 mg/ml | 1.0 mg/ml | Physiological saline |
| 2 | DSPE-020CN | 15 mg/ml | 1.0 mg/ml | Water |
| 3 | CS-020 | 15 mg/ml | 1.9 mg/ml | Physiological saline |
| 4 | DSPE-020GL2U | 15 mg/ml | 1.35 mg/ml | Physiological saline |
| 5 | CS-010 | 15 mg/ml | 1.75 mg/ml | Physiological saline |
| 6 | CS-010 | 15 mg/ml | 1.9 mg/ml | Physiological saline |
| 7 | CS-010 | 15 mg/ml | 3.0 mg/ml | Physiological saline |

It should be noted that the aqueous solutions of Working Examples 1, 2, 5 and 6 did not become whitish and form a deposit and a precipitate at 4° C. or room temperature for at least 2 months, and it was confirmed that the aqueous solutions were excellent in storage stability. Moreover, the aqueous solution of Working Example 3 did not become whitish and form a deposit and a precipitate at 4° C. for at least 2 months, and it was confirmed that the aqueous solution was excellent in storage stability. Furthermore, the aqueous solution of Working Example 7 did not become whitish and form a deposit and a precipitate at 4° C. for at least 1 month, and it was confirmed that the aqueous solution was excellent in storage stability.

Confirmation Example 1: Pharmacokinetic Study Using Aqueous Solution Obtained in Working Example 1

The aqueous solution obtained in Working Example 1 was filtered and sterilized with Millex (registered trademark)-

GV (0.22 μm; available from Millipore Japan Corporation/Merck Millipore Corporation) and intravenously administered to female and male Sprague-Daweley IGS rats (6 weeks old) to investigate the pharmacokinetics of Compound (I).

Testing Method

As groups of animals, female and male Sprague-Daweley IGS rats (available from Charles River Laboratories Japan, Inc.) were used. The rats were 6 weeks old. The male rats had body weights of 166 to 189 g, and the female rats had body weights of 123 to 145 g.

The rats were quarantined and acclimated in a SPF (specific pathogen free) laboratory for animal experimentations for seven days, and their states of health were simultaneously observed. Each of the rats was kept in a sterilized stainless cage. In the SPF laboratory for animal experimentations, the temperature was maintained at 20.6 to 22.5° C., and the relative humidity was maintained at 44 to 60%. In the SPF laboratory for animal experimentations, ventilation was provided fifteen times per hour. Regarding illumination in the SPF laboratory for animal experimentations, a bright state and a dark state were switched every 12 hours.

As foods for rats, a standard dry food in stick-shape (whose components were already analyzed) was used. As drinking water, tap water which was confirmed to be within a range of the reference value was used, and the rats were allowed to freely drink it.

The above-mentioned quarantined rats were randomly divided into the following three groups (four female rats and four male rats per group) by weight.

(1) Group 1: the aqueous solution obtained in Working Example 1 was administered in a dose of 1 mL/kg.

(2) Group 2: the aqueous solution obtained in Working Example 1 was administered in a dose of 2 mL/kg.

(3) Group 3: the aqueous solution obtained in Working Example 1 was administered in a dose of 3 mL/kg.

After the quarantined rats fasted overnight (for about 16 hours), the aqueous solution obtained in Working Example 1 was intravenously administered. Blood was collected 0.083 hours, 0.25 hours, 0.5 hours, 1 hour, 4 hours, and 24 hours after the administration, and the concentration of Compound (I) in the blood was measured. The maximum blood concentration, $C_0$ (ng/mL), just after the composition for injection was intravenously administered, and the area under the blood concentration-time curve of Compound (I) over 0 to 24 hours after the administration, $AUC_{0-24}$ (ng·h/mL), were calculated from the measured concentrations of Compound (I) in the blood at the collection times.

Testing Results

The following table shows the average values of $C_0$ and $AUC_{0-24}$ of three male rats selected from the respective administration groups.

TABLE 2

|  | Group 1 | Group 2 | Group 3 |
| --- | --- | --- | --- |
| Dose of Compound (I) | 1 mg/kg | 2 mg/kg | 3 mg/kg |
| $C_0$ (ng/mL) | 1383.37 | 3205.93 | 4846.28 |
| $AUC_{0-24}$ (ng · h/mL) | 304 | 620 | 1263 |

The following table shows the average values of $C_0$ and $AUC_{0-24}$ of three female rats selected from the respective administration groups.

TABLE 3

|  | Group 1 | Group 2 | Group 3 |
| --- | --- | --- | --- |
| Dose of Compound (I) | 1 mg/kg | 2 mg/kg | 3 mg/kg |
| $C_0$ (ng/mL) | 2149.95 | 2823.27 | 5246.73 |
| $AUC_{0-24}$ (ng · h/mL) | 388 | 540 | 981 |

The results of these confirmation examples clearly showed that when the aqueous solution obtained in Working Example 1 was intravenously administered, Compound (I) serving as an efficacious component in vivo could be exposed in a dose-dependent manner and in a sufficient amount. Moreover, in these confirmation examples, no rats died, and no toxicity that may cause a critical disorder or the like was observed.

The invention claimed is:

1. A method for manufacturing a formulation comprising:
preparing a dissolution liquid obtained by dissolving a compound represented by Formula (I):

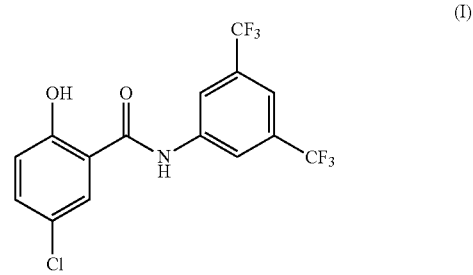 [SMILES: O=C(Nc1cc(C(F)(F)F)cc(C(F)(F)F)c1)c1cc(Cl)ccc1O]

or a pharmacologically acceptable salt thereof, and a compound represented by any of Formulas (II) to (IV):

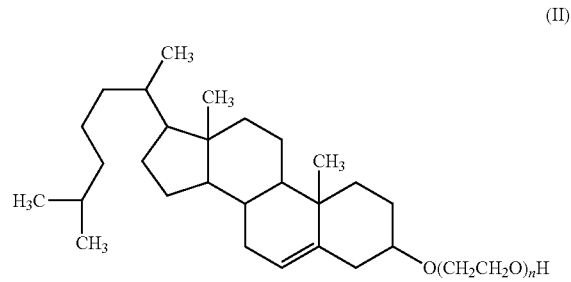

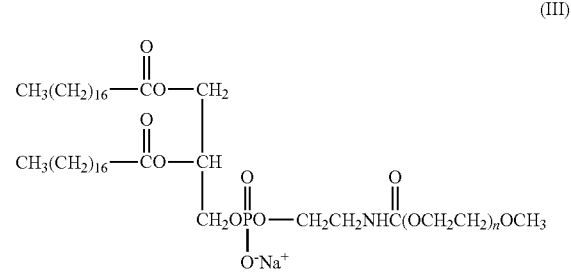

-continued

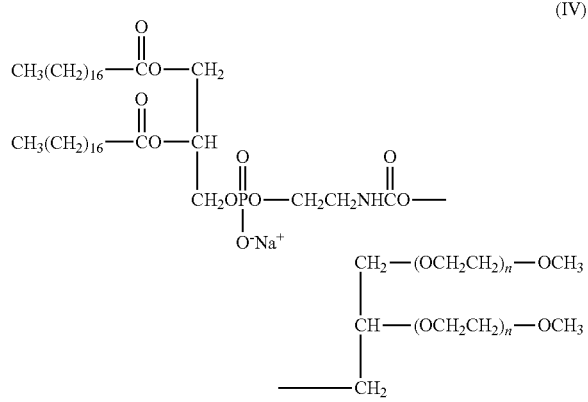

in an organic solvent comprising one or more of an alcohol, dimethylsulfoxide (DMSO), methyl tert-butyl ether, N,N-dimethylacetamide, N,N-dimethylformamide, acetone, N-methyl-2-pyrrolidone, tetrahydrofuran, acetonitrile, or ethyl acetate;
removing the organic solvent from the dissolution liquid in order to obtain a residue; and
adding an aqueous solution to the residue to dissolve the residue; wherein
in Formula (II), n is 14 to 37,
in Formula (III), n is 22 to 46, and
in Formula (IV), n is 22 to 46.

2. The method for manufacturing a formulation according to claim 1, wherein n in the compound represented by Formula (II) is 14 or 37.

3. The method for manufacturing a formulation according to claim 1, wherein n in the compound represented by Formula (III) is 22 or 46.

4. The method for manufacturing a formulation according to claim 1, wherein n in the compound represented by Formula (IV) is 22 or 46.

5. A formulation obtained through the method according to claim 1.

6. A formulation obtained through the method according to claim 2.

7. A formulation obtained through the method according to claim 3.

8. A formulation obtained through the method according to claim 4.

9. The method for manufacturing a formulation according to claim 1, wherein the alcohol is methanol, ethanol, isopropanol, or tert-butanol.

10. The method for manufacturing a formulation according to claim 1, wherein the organic solvent is ethanol.

11. The method for manufacturing a formulation according to claim 1, wherein the aqueous solution is water, physiological saline, aqueous solution of glucose, Ringer's solution, or lactated Ringer's solution.

12. The method for manufacturing a formulation according to claim 1, wherein the aqueous solution is water or physiological saline.

13. The method for manufacturing a formulation according to claim 9, wherein the aqueous solution is water, physiological saline, aqueous solution of glucose, Ringer's solution, or lactated Ringer's solution.

14. The method for manufacturing a formulation according to claim 9, wherein the aqueous solution is water or physiological saline.

15. The method for manufacturing a formulation according to claim 10, wherein the aqueous solution is water, physiological saline, aqueous solution of glucose, Ringer's solution, or lactated Ringer's solution.

16. The method for manufacturing a formulation according to claim 10, wherein the aqueous solution is water or physiological saline.

17. The method for manufacturing a formulation according to claim 1, wherein a temperature of the aqueous solution is from 4 to 60° C.

18. The method for manufacturing a formulation according to claim 9, wherein a temperature of the aqueous solution is from 4 to 60° C.

19. The method for manufacturing a formulation according to claim 10, wherein a temperature of the aqueous solution is from 4 to 60° C.

20. The method for manufacturing a formulation according to claim 11, wherein a temperature of the aqueous solution is from 4 to 60° C.

21. The method for manufacturing a formulation according to claim 12, wherein a temperature of the aqueous solution is from 4 to 60° C.

22. The method for manufacturing a formulation according to claim 13, wherein a temperature of the aqueous solution is from 4 to 60° C.

23. The method for manufacturing a formulation according to claim 14, wherein a temperature of the aqueous solution is from 4 to 60° C.

24. The method for manufacturing a formulation according to claim 15, wherein a temperature of the aqueous solution is from 4 to 60° C.

25. The method for manufacturing a formulation according to claim 16, wherein a temperature of the aqueous solution is from 4 to 60° C.

26. A formulation comprising:
a compound represented by Formula (I):

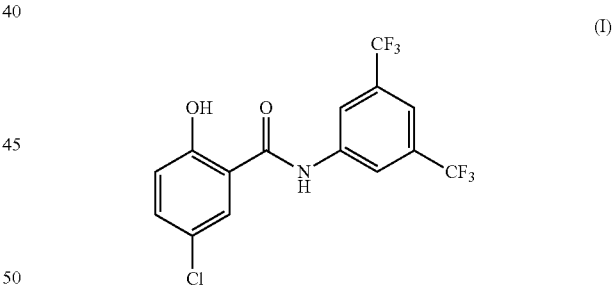

or a pharmacologically acceptable salt thereof, and
a compound represented by any of Formulas (II) to (IV):

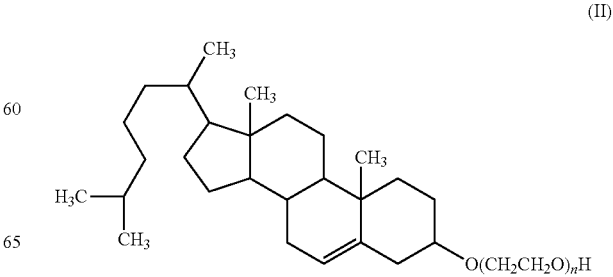

-continued
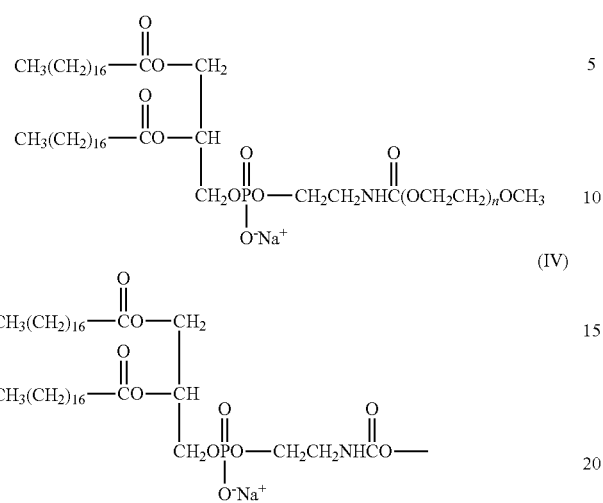
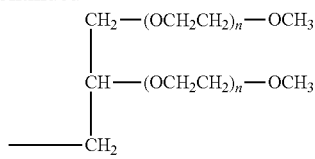
wherein
in Formula (II), n is 14 to 37,
in Formula (III), n is 22 to 46, and
in Formula (IV), n is 22 to 46,
dissolved in an aqueous solution comprising water, physiological saline, aqueous solution of glucose, Ringer's solution, or lactated Ringer's solution.
27. The formulation according to claim 26, exhibiting a storage stability of at least 2 months when stored at 4° C.
* * * * *